(12) United States Patent
Hubac (10) Patent No.: US 10,809,163 B2
(45) Date of Patent: Oct. 20, 2020

(54) DEVICE FOR COLLECTING BIOLOGICAL MATERIAL FROM A BIOLOGICAL TRACE

(71) Applicant: L'ETAT FRANCAIS REPRESENTE PAR LE MINISTERE DE L'INTERIEUR, Issy les Mulineaux (FR)

(72) Inventor: Sylvain Hubac, Cergy Pontoise (FR)

(73) Assignee: L'ETAT FRANCAIS REPRESENTE PAR LE MINISTERE DE L'INTERIEUR, Issy les Mulineaux (FR)

( * ) Notice: Subject to any disclaimer, the term of this patent is extended or adjusted under 35 U.S.C. 154(b) by 159 days.

(21) Appl. No.: 15/551,227

(22) PCT Filed: Feb. 17, 2016

(86) PCT No.: PCT/FR2016/000026
§ 371 (c)(1),
(2) Date: Aug. 15, 2017

(87) PCT Pub. No.: WO2016/132028
PCT Pub. Date: Aug. 25, 2016

(65) Prior Publication Data
US 2018/0038774 A1 Feb. 8, 2018

(30) Foreign Application Priority Data
Feb. 20, 2015 (FR) ...................... 15 00350

(51) Int. Cl.
*G01N 1/02* (2006.01)
*B01L 3/00* (2006.01)
*C12Q 1/6869* (2018.01)

(52) U.S. Cl.
CPC .............. *G01N 1/02* (2013.01); *B01L 3/5029* (2013.01); *C12Q 1/6869* (2013.01);
(Continued)

(58) Field of Classification Search
CPC ................................. G01N 1/02; B01L 3/5029
(Continued)

(56) References Cited

U.S. PATENT DOCUMENTS

2005/0023853 A1 10/2005 Knezevic
2011/0004122 A1 1/2011 Sangha
(Continued)

FOREIGN PATENT DOCUMENTS

WO 88/04431 6/1988

*Primary Examiner* — Jezia Riley
(74) *Attorney, Agent, or Firm* — Arrigo, Lee, Guttman & Mouta-Bellum LLP (57) ABSTRACT

A device for collecting biological material, characterized in that it comprises a rod having, at one end, a dry absorbent body having a surface area of between approximately 1 and approximately 3.14 mm², said absorbent body comprising surfactants and denaturing agents. The present invention also relates to the use of said device for sampling biological material from a biological trace having any surface area greater than a micro surface area of around 1 mm² or having any volume greater than a micro-volume of around 1 microliter, and to a method for collecting biological material and a method for collecting and analyzing and/or identifying biological material, comprising a step of putting said device in contact with said biological material.

11 Claims, 7 Drawing Sheets

(52) U.S. Cl.
CPC ... *B01L 2200/141* (2013.01); *B01L 2300/069* (2013.01); *B01L 2300/0832* (2013.01); *G01N 2001/027* (2013.01); *G01N 2001/028* (2013.01)

(58) Field of Classification Search
USPC .......................................................... 435/6.12
See application file for complete search history.

(56) References Cited

U.S. PATENT DOCUMENTS

2012/0027112 A1   10/2012   Battrell
2014/0083213 A1   3/2014    Triva

Figure 1 A grip / handling area    rod    absorbent body scored point

Figure 1B

Case

Figure 2 A

Schema of the collection device

Grip / handling area

________ Straight rod

Identifiable case

▐▌ : Bar code

▒▒▒ : Text zone

╱ Scored or ejectable collection surface for direct analysis

Figure 2 B

Schema of the double collection device

Grip / handling area

________ Straight rod

Identifiable case

▐▌ : Bar code

▒▒▒ : Text zone

Scored or ejectable collection surface for direct analysis

Scored or ejectable collection surface for storage

Figure 3

Schema of the double collection device

Table 1 AmpFℓSTR® Identifiler® PCR Amplification Kit 200 reactions (Part no. 4322288)

| Part no. | Part | Storage Conditions |
|---|---|---|
| 361680 | AmpFℓSTR® PCR Reaction Mix, 2 tubes, 1.1 mL/tube | −15 to −25°C upon receipt. |
| | Contains $MgCl_2$, dATP, dGTP, dCTP, and dTTP, bovine serum albumin, and 0.05% sodium azide in buffer and salt. | 2 to 8°C after initial use. |
| 361676 | AmpFℓSTR® Control DNA 9947A, 1 tube, 0.3 mL | |
| | Contains 0.1 ng/μL human cell line DNA in 0.05% sodium azide and buffer. The profile of this female DNA is CSF1PO 10, 12; D2S1338 19, 23; D3S1358 14, 15; D5S818 11, 11; D7S820 10, 11; D8S1179 13, 13; D13S317 11, 11; D16S539 11, 12; D18S51 15, 19; D19S433 14, 15; D21S11 30, 30; FGA 23, 24; TH01 8, 9.3; TPOX 8, 8; vWA 17,18. | |
| 4322292 | AmpFℓSTR® Identifiler® Primer Set, 1 tube, 1.1 mL | −15 to −25°C upon receipt. |
| | Contains locus-specific 6-FAM™, VIC®, NED™, and PET® dye-labeled and unlabeled primers in buffer. The primers amplify the STR loci CSF1PO, D2S1338, D3S1358, D5S818, D7S820, D8S1179, D13S317, D16S539, D18S51, D19S433, D21S11, FGA, TH01, TPOX, vWA, and the gender marker Amelogenin. | 2 to 8°C after initial use. Store protected from light. |
| 4373672 | AmpFℓSTR® Identifiler® Allelic Ladder, 1 tube, 0.05 mL | −15 to −25°C upon receipt. |
| | Contains the following amplified alleles:<br>• 6-FAM™ dye (blue): D8S1179 8–19; D21S11 24, 24.2, 25–28, 28.2, 29, 29.2, 30, 30.2, 31, 31.2, 32, 32.2, 33, 33.2, 34, 34.2, 35, 35.2, 36–38; D7S820 6–15; CSF1PO 6–15.<br>• VIC® dye (green): D3S1358 12–19; TH01 4–9, 9.3, 10, 11, 13.3; D13S317 8–15; D16S539 5, 8–15; D2S1338 15–28.<br>• NED™ dye (yellow): D19S433 9–12, 12.2, 13, 13.2, 14, 14.2, 15, 15.2, 16, 16.2, 17, 17.2; vWA 11–24; TPOX 6–13; D18S51 7, 9, 10, 10.2, 11–13, 13.2, 14, 14.2, 15–27.<br>• PET® dye (red): Amelogenin X, Y; D5S818 7–16; FGA 17–26, 26.2, 27–30, 30.2, 31.2, 32.2, 33.2, 42.2, 43.2, 44.2, 45.2, 46.2, 47.2, 48.2, 50.2, 51.2. | 2 to 8°C after initial use. Store protected from light. IMPORTANT! The allelic ladder contains PCR products. Do not amplify. To avoid contamination, store the allelic ladder separate from the other kit components and unamplified DNA. |
| 4385214 | AmpliTaq Gold® DNA Polymerase, 2 tubes, 0.05 mL/tube, enzyme activity 5 U/μL | −15 to −25°C. |

Figure 6A  Comparison of the average fluorescence intensities obtained from 1 µl of blood collected using a cellulose disk and a standard swab Figure 6B  Comparison of mean fluorescence intensities obtained from 5 µl of blood collected using a cellulose disk and flocked synthetic fibers Figure 6C  Comparison of mean fluorescence intensities obtained from 1µl of sperm collected using a cellulose disk and flocked synthetic fibers

Figure 7

Flocked fiber device of 1.13 mm² surface 5 microliters of blood

Figure 8

Collection with a flocked fiber device of 1.13 mm² surface

Collection with a standard swab

Figure 9

Flocked fiber device of 1.13 mm² surface

Barrel of a gun

DEVICE FOR COLLECTING BIOLOGICAL MATERIAL FROM A BIOLOGICAL TRACE

The present invention relates to a device for collecting biological material, allowing the sampling of biological material, its analysis and its identification in a rapid manner, without the need for an extraction step before the steps of amplification, analysis and identification of said biological material. In particular, this device may be used in the field of security, for example in the context of technical and scientific police investigations for the purpose of genetic analysis or for identification by DNA fingerprinting.

To date, the collection devices (commonly referred to as sampling kits or collection kits) of biological material are made of standardized swabs (such as the FloqSwabs 4N6 Crime Scene Cat 3509C, Regular tip in plain tube marketed by the company Copan), variants of them being describe in patent application US 2014/0083213. They take the form of a rod, the end of which is covered with flocked nylon fibers, creating a zone for collecting the biological material on the order of 1 cm$^2$.

These swabs are used in the many fields that require the collection and analysis of biological materials such as the field of medical analysis, or bacteriological analyzes for example in the food, cosmetic, environmental and pharmaceutical fields. These swabs are also traditionally used by police forces, for example on crime scenes for genetic analysis or identification by genetic fingerprint.

However, these swabs have many disadvantages. First of all, these swabs do not allow to collect biological material from biological trace, in particular in case of micro-trace, i.e. having a micro-surface of the order of 1 mm$^2$ or presenting a micro-volume of the order of 1 microliter. The patent application US 2014/0083213 indicates that these standard swabs could only be used from a volume of 5 microliters, and it is in fact not recommended for the collection of biological material of such a small volume. Furthermore, even on surfaces or volumes in the order of 5 mm2 or 5 microliters, using such swabs alter the biological trace, making it difficult or impossible a second sample if necessary or other analyses, such as analysis and identification of the papillary pattern of the fingerprints in the case of a contact trace, or determining the biological nature of the trace.

In addition, the methods of collecting and analyzing and/or identifying biological material using these swabs require many steps, and in particular at least one step of cell lysis and extraction of the nucleic acids, for example DNA, before amplification with sometimes a step of stabilizing the reaction of amplification before being able to carry out the analysis of the nucleic acid amplification products. Each of the analysis steps must be performed in a laboratory environment and also require specialized technical staff, premises and dedicated hardware. The steps of analysis and identification, in particular the step of extraction which is very contaminating of said nucleic acids, requires a protected environment from contaminations. These constraints exclude the use of a standard analyzer outside the protected perimeter of a conventional laboratory. These conditions are governed by the European recommendations of ENFSI (European Network of Forensic Science Institutes) in its quality assurance program of the working group treating DNA. The duration of the analyses is typically about ten hours to obtain the result of several dozens of biological samples of traces taken from scenes of offense (eg, crime scene).

These swabs require a large amount of reagents for cell lysis and extraction, and then for amplification of the nucleic acids, said reagents being extremely expensive. Furthermore, these steps must be carried out in an analysis laboratory. All this makes use of these swabs and methods of collection and for analyzing and/or identifying biological material using said swabs being long, likely to be subject to contaminations and mishandling errors, in particular during the transfer from the collection site of the biological material to the analysis laboratory, and of course expensive.

Thus, there is today a need for biological material collection devices allowing, with at least equal efficiency as to the collection but also the analysis and/or identification of said biological material collected with said devices,
to secure the collected biological material with a minimization of the risk of contamination,
to enable the collection of biological material in the state of micro-trace or micro-volume,
to reduce the amount of biological material taken for, especially in the case where the biological material is present as a trace, to not alter entirely or a minimum of said biological trace, especially in the case of fingerprints;
to prevent the loss of nucleic acids from the collected biological material as is the case in the conventional step of cell lysis and extraction;
to minimize usage costs;
to minimize the time required between the collection and the analysis result and/or the identification of the biological material;
To enable accurate collection of biological material in difficult access areas, in particular small-diameter orifices capable of presenting microtraces, such as the barrel of a firearm, for example of a diameter of 4.5 mm, or a bone cavity such as a section of human rib taken from a forensic pathway for the identification of disaster victims.

Recent developments in DNA analysis as soon as possible after the collection of biological material do not offer real "all in one" tools allowing to achieve this objective and do not have advantages over conventional swabs and analysis methods.

The applicant has developed the devices, as well as the method of collection, analysis and/or identification using them, object of the present invention, which solve the whole technical problem. In particular, the device according to the invention makes it possible to reduce the alteration of the biological trace by a less sampling surface, to significantly reduce laboratory analysis time, to reduce the contamination obstacle by removing the step of extracting the nucleic acids, in particular DNA, between the sample and the transition to analyzer and therefore allowing the use of a serial analyzer of nucleic acids out of the conventional genetic laboratory thereby providing a mass analysis capability closest to the sampling scene. By this collection and analysis method, the delay between the collection of the biological trace and the determining of the genetic profile is less than three hours for the first twenty-one collected biological traces. The analysis system then generates at least twenty and one additional results every twenty to twenty-five minutes.

The device according to the invention allows, on the one hand, to obtain much faster results than in the context of a conventional laboratory analysis and on the other hand enables the use of one DNA analyzer outside the conventional genetic laboratory, either as close as possible to a crime scene in a mobile laboratory, either within a local judicial police service. Thus, the time for obtaining the results is considerably reduced while maintaining the advantages of a series analysis production of several tens of samples.

Moreover, the use of this collection tool, object of the present invention allows to reduce the cost of the manpower, equipments and laboratory consumables needed for genetic analysis.

The device according to the invention is particularly intended for design and industrialization of a universal biological material sampling device, very easy to use, especially by technical and scientific police practitioners of first level, likely of using it for the taking of samples for private or public laboratories or institutions.

A first object of the present invention is a biological material collection device, characterized in that it comprises a rod having at least at one end a dry absorbent body having a surface area of between about 1 and about 3.14 mm2, said absorbent body comprising surfactants and denaturing agents.

According to the present invention, biological material is meant to designate any material from a living being, may be in the form of molecules, organelles, fluids, cell fragments or cells, and present on a biological or non-biological support.

By biological support is meant a biological sample, which can be derived from all or part of a living organism, which may or may not be dead at the time of collection, for example a human being.

A non-biological support is meant to designate according to the present invention a non-living surface such as an object or an inert structure. These surfaces provide environmental samples that, in the absence of contact or contamination with biological material from a living being, are free of nucleic acids in contrast to biological supports. Thus, samples obtained from non-biological media containing nucleic acid traces are the result of a contact or contamination by a biological organism that the present device can collect, analyze and identify. These non-biological media may be of any nature and, for example, in the case of using the collection device according to the invention by the police forces on a crime scene, it may typically be a portable phone, a door handle, the trigger tail or the inside of the barrel of a weapon, or a cup.

The device according to the present invention is particularly useful for the collection of biological material present on a non-biological support, in an environment where many contaminants are present, such as, for example, a crime scene where police forces are to perform an identification of biological material, and this especially as the biological material is in the form of biological microtraces.

Preferably, said biological material comprises nucleic acids, preferably DNA, in a form allowing their amplification by PCR (Polymerase Chain Reaction) and their analysis and/or identification. The biological material is advantageously selected from the group consisting of physiological body fluids, cells or suspensions of humans or animals, in particular a contact trace, blood, bone marrow, buccal cells, degraded or non-degraded human biological tissue or cell suspensions of plants; liquid products, extracts or suspensions of bacteria, fungi, plasmids, parasites, or viruses; liquid extracts or homogenates of human or animal body tissues; media derived from nucleic acid synthesis; and chemically or biochemically synthesized nucleic acid mixtures. Preferably, said material is selected from the group consisting of physiological body fluids, cells or suspensions of humans or animals. In a particularly preferred manner, the biological material according to the present invention is in particular a contact trace, blood, bone marrow, buccal cells, degraded or undegraded human biological tissue.

According to the present invention, nucleic acids mean DNA and RNA. Preferably, according to the present invention, we intended to mean DNA. According to the present invention, a rod preferably intends to mean a rod having a length of between about 5 cm and about 20 cm, more preferably between about 5 cm and about 10 cm. Advantageously, the rod has a diameter of the order of 1 mm. Advantageously, the rod is rectilinear. The rod can be made of any suitable material according to the general knowledge of the person skilled in the art, and can in particular be made of polypropylene-type plastic. Preferably, according to the invention, the rod is flexible.

According to one aspect of the invention, one end of the rod serves as a zone for gripping and manipulating the device, whereas the other end comprises the absorbent body and serves for the collection of biological material.

According to a second aspect of the invention, the rod comprises an absorbent body at each end, and the area for gripping and manipulating the device is located in the middle of the rod.

Per absorbent body is meant according to the present invention a dry solid support made of an absorbent, natural or synthetic material. Preferably, said absorbent body is selected from the group consisting of cellulose, nitrocellulose, cotton, flocked synthetic fibers, such as flocked nylon fibers, hydrophilic polymers, glass fiber, polytetrafluoroethylene, polyester, nylon, rayon, cotton, and porous ceramic. More preferably, the absorbent body is selected from cellulose, and flocked synthetic fibers. In a particularly preferred manner, said absorbent body is composed of flocked synthetic fibers, preferably flocked Nylon fibers, preferably directly onto the rod. Advantageously, the fibers are adhered to the rod. Preferably, the fibers measure between 1 and 1.5 mm in length and between 0.01 and 0.5 mm in diameter. This configuration allows to obtain the best results in terms of collecting biological material and salting out the nucleic acids of said biological material, associated with simplicity of manufacture and use.

According to one aspect of the invention, the synthetic fibers are flocked directly onto the rod, preferably a flexible rod. In another aspect of the invention, the synthetic fibers are flocked onto a pellet, preferably a flexible pellet, the flexibility of which is suitable for adapting to the surface state of the object support of the specimen, said pellet being attached to the rod. Preferably the pellet is made of a flexible plastic, for example polypropylene.

Advantageously according to the invention, the synthetic fibers of the device according to the invention enable the trapping of the nucleic acids of said biological material, in particular DNA, and then release it in a liquid medium, in particular aqueous, such as a PCR amplification reaction mixture of nucleic acids.

Advantageously, when the absorbent body is composed of synthetic fibers, preferably Nylon, flocked, amplification of nucleic acids by PCR can be performed either by conserving the absorbing body in the PCR amplification reaction medium of nucleic acids and in the thermocycler, either by contacting the absorbent body with the nucleic acid PCR amplification reaction medium, by stirring and then removing said absorbent body, allowing to release said nucleic acids into said medium.

Advantageously, the absorbent body is flexible, which facilitates the collection of biological material. The flexibility of the rod makes it possible to adapt to the surface state of the object support of the sample.

The absorbent body according to the present invention has a surface area of from about 1 to about 3.14 mm2.

It can thus be a disc of 1, 2 mm diameter, corresponding to a surface 1.13 mm2, or a 2 mm diameter disc corresponding to a surface of 3, 14mm2.

In particular, if the collection is performed on a wet biological material, and thus there is no step of wetting the biological material or the absorbent body prior to collection, more the surface will be reduced, better will be the results of analysis and identification of the nucleic acids, in particular of the DNA of the collected biological material.

By way of example, mention may be made of several types of absorbent bodies according to the invention, the surface area of which is of the order of 1 to 3.14 mm$^2$, namely:

1-2 mm$^2$ in its form of synthetic fibers flocked on a rod;
About 1.13 mm$^2$ in its form of a cellulose pellet of 1.2 mm diameter;
About 1.13 mm$^2$ in the form of flocked synthetic fibers on a 1.2 mm diameter pellet;
About 3.14 mm$^2$ in the form of a 2 mm-diameter cellulose pellet;
About 3.14 mm$^2$ in the form of synthetic fibers flocked on a 2 mm-diameter pellet.

In every case, the use of the rapid collection and analysis device, due to its low contact and wiping surface of the biological trace, preserves at most genetic material present on the wiped media, which could be use either in another new sample, either of an operation of another nature such as identifying the papillary pattern of the digital traces or determining the biological nature of the trace, for example.

Thanks to its miniature surface area in the range of 1 to 3.14 mm$^2$, the absorbent body presents another major economic interest, because this feature allows to carry out the amplification of nucleic acids in a reduced reaction volume of 50% with respect to the supplier's recommended conditions and thus to reduce considerably the cost of analyses of a large number of samples. In fact, tests performed with the Identifiler plus and Globalfiler gene amplifications kits have allowed by example to demonstrate the efficacy of the device for a PCR reaction volume of 25 µl as recommended by the provider, but also in half-reduced reaction volume of 12.5 µl.

It has been demonstrated that such a small surface of the absorbent body enables a sufficient amount of nucleic acids to be collected to obtain a genetic profile.

The absorbent body is pre-treated with denaturing agents and surfactants in its design thereby allowing in situ lysis of the cells. It is therefore not necessary to apply to this absorbent body a specific humidification pad for the lysis of the cells upstream of the collection.

According to the present invention, surfactants and denaturing agents mean agents for cell lysis, protein denaturation and nucleic acid extraction. The surfactants and denaturing agents may be selected from a list comprising uric acid or urate salt, tris, SDS-PAGE, preferably guanidine thiocyanate, Triton X100, Tween 20, CHAPS, CHAPS-O, octylglucoside, octyl thioglucoside, and combinations thereof.

Preferably according to the invention, surfactants and denaturing agents are a combination of uric acid or urate salt, tris, and SDS. Preferably, the absorbent body further comprises EDTA.

In particular, the absorbent body comprises a mixture per cm$^2$ of 2 uric acid micromols, 8 micromols of Tris, and 1 mg of SDS. Preferably, the absorbent body further comprises 0.5 micromols of EDTA.

According to a variant of the invention, the surfactants and denaturing agents may be a combination of guanidine salt, preferably guanidine thiocyanate, and Triton XI 00. An effective amount of said agents can be found between 0.01 M: 0.01 M and 0.4 M: 0.4 M, Alternatives denaturing agents and surfactants, according to the general knowledge of the person skilled in the art, can be used in the absorbent body in order to ensure its safety with respect to human and animal health, if for example the device should be used on living organisms, for example for medical analysis purposes. In these conditions, the absorbent body may, for example, be applied directly to the buccal cavity of an individual in order to sample cells for genetic analyses.

Regardless of its shape and nature, the absorbent body thus comprises surfactants and denaturants has the property of trapping and then releasing the collected nucleic acids thus made directly available, without delay, for molecular biology applications without the need for a conventional laboratory extraction step.

According to a preferred embodiment of the present invention, said end having said absorbent body of the device is scored or ejectable.

In a particularly preferred manner, the end is scored. This can be achieved, for example, with a cross-sectional point on the rod, in the form of a thinner region on the rod, allowing to cut the rod by a pressure, greater than when collecting biological material, on the end bearing the absorbent body. Preferably this cross-sectional point is at a height allowing the total insertion of the absorbent body and the cut rod into a container. Preferably this cross-sectional point is between 0.5 mm and 2 mm, even more preferably 1.7 mm.

According to a preferred embodiment of the present invention, said device comprises a hermetic case in which the entire device is inserted, or a portion of the rod and the end of the rod with the absorbent body, excluding the gripping and handling area, or only the absorbent body. Preferably, the hermetic case includes a unique identifier, such as a bar code, RFID, or NFC. Preferably the unique identifier according to the invention is a bar code.

Figure 1:
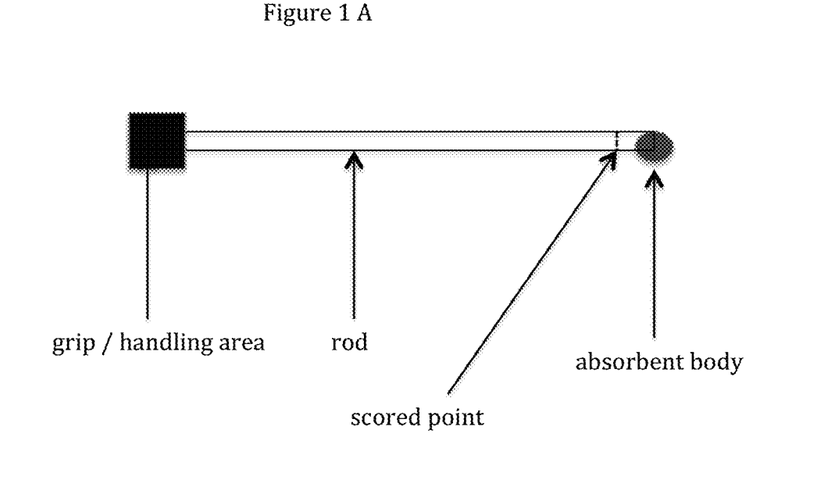
FIG. 1A represents, in cross-section, the collection device of the invention, outside its case. The gripping and handling area is at one end and the absorbent body is at an opposite end.
FIG. 1B represents the collection device in its case, before or after collection of the biological material with an absorbent body in the rectilinear extension of the rod.
Figure 1B:
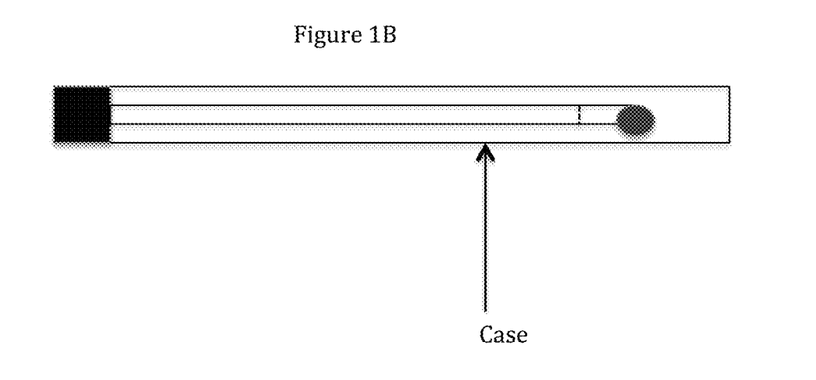
Figure 2:
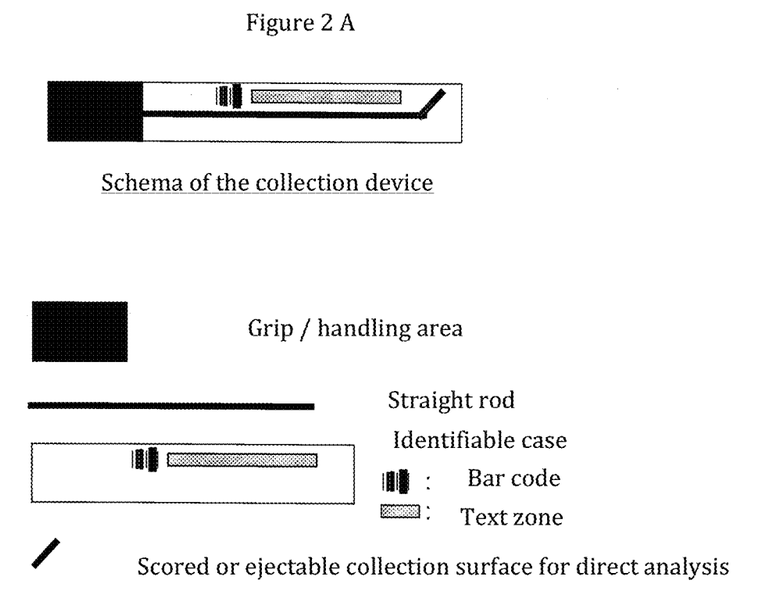
FIG. 2 shows the collection device with an absorbent body (referred to as "collection surface") having an angle with respect to the straight rod to facilitate collection, and its sealed case identifiable by a bar code.
Figure 3:
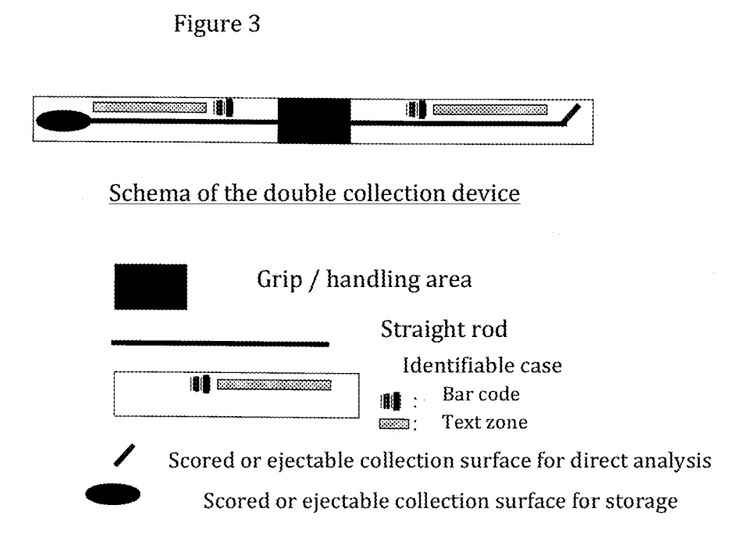
FIG. 3 shows a variant of the collection device or a second a collection device presenting a second absorbent body (referred to as a collection surface for preservation) is coupled to the first device as shown in FIG. 2. The gripping area is located in the middle of the rod and not at its end.
Figure 4:
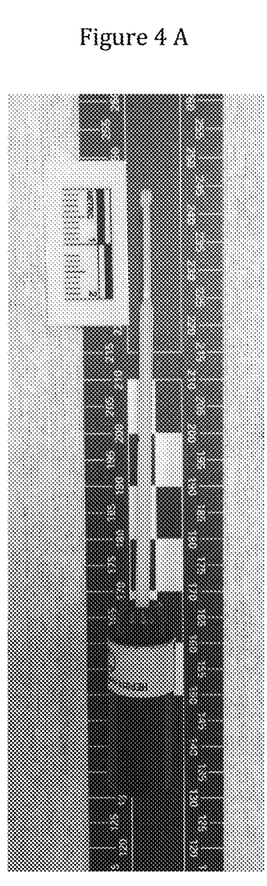
FIG. 4A is a photograph of the device with an absorbent body of a surface of 3. 14 mm$^2$, composed of nylon fibers flocked on the rod.
FIG. 4B is a photograph of the device with an absorbent body having a surface of 1.13 mm$^2$, composed of flocked nylon fibers on the rod.
FIG. 4C is a photograph of a standard FloqSwab 4N6 Crime Scene Cat 3509C, Regular tip in plain tube swab, marketed by the Copan company.

According to a variant of the invention illustrated in FIG. 3, this device can also be coupled to a second collection device consisting of a rod, preferably of a length of from about 5 to about 10 cm, the end of which is preferably scored or ejectable, has an absorbent body for collecting biological material. This second collection device can, for example, allow for the preservation and subsequent extraction of nucleic acids for analyses by molecular biology techniques, in particular by PCR. In this configuration, both devices are associated but each inserted into a separate hermetic case, preferably identifiable by a bar code, RFID or NFC.

The absorbent body of this second collection device may be of the same or different size and/or composition from the absorbent body of the first device. Preferably, said absorbent body of the second device consists of synthetic fibers flocked to the rod or of cotton fibers wound around the rod, of a surface area between 1 mm$^2$ and 2 cm$^2$.

Advantageously, according to the invention, the collection device and in particular its absorbent body, is subjected at the end of its manufacture and before its use a treatment by any type of dry sterilization system, especially of the gamma irradiation type, oxidized ethylene and plasma. This sterilization treatment prevents before use contamination of the collection device by biological material other than that which will be taken. This allows the collection device to respond to the most demanding international recommendations for preventing contamination by nucleic acids not coming from the taken biological trace.

The particularly preferred device according to the invention has a solid and dry absorbent body made of synthetic fibers flocked on the rod, of a surface of between about 1 and about 3.14 mm$^2$, scored, on a rectilinear rod of 5 to 10 cm long, associated with an identifiable hermetic case. The absorbent body comprises 2 uric acid micromols, 8 Tris micromols, 0.5 micromols of EDTA and 1 mg of SDS per cm$^2$. This particularly preferred device is used without prior humidification of the biological material or of the absorbent body prior to collection.

A second object of the present invention is a kit for collection, analysis and/or identification of biological material comprising a device according to the invention, two containers, at least one PCR amplification reaction mixture of nucleic acids, a thermocycler, a sequencing reaction mixture, and a sequencer.

Preferably, according to the invention, said kit can be used in a mobile laboratory, such as a mobile vehicle, for example of the van or bus type.

Preferably according to the invention, the container consists of the one or more wells of a plate or a bar, for example of 8 wells, 96 wells or 384 wells and is ready for use for PCR. Thus, preferably, the first container is prefilled with the nucleic acids PCR amplification reaction mixture. Advantageously, said container also comprises the amplification reaction controls, prefilled in the container and already added into the ready-to-use amplification mixture. The second container is preferably prefilled with the sequencing reaction mixture of the nucleic acid PCR amplification products. Advantageously, said container may also be prefilled, in addition to mixing the sequencing reaction, with a set of reference DNA fragments, commonly referred to as allelic ladder, allowing identification of the amplifications products.

A container means a container for the absorbent body for contacting said absorbent body with the amplification reaction mixture by PCR of nucleic acids and the PCR and contacting the amplification products with the sequencing reaction mixture. For example, it is meant according to the present invention a container having a capacity of 10 to 350 microliters, or a combination of containers having a capacity of 10 to 200 microliters, such as a 96-well, or 384-well PCR microplate. Preferably, the container is a 96-well PCR microplate of 100 or 200 microliters.

A third object of the present invention relates to a mobile laboratory for collection, analysis and/or identification of biological material comprising a kit according to the invention in a motorized mobile vehicle.

Said powered mobile vehicle is typically a van or a bus. Preferably said vehicle is electrically self-contained, for example with a device ensuring uninterrupted power supply throughout the PCR amplification process and sequencing. Preferably, the vehicle has a secure telematics connection for transmitting the information in any point of the earth globe, and in particular the genetic profiles thus determined, for example to an expert or in the national or international databases.

Said mobile laboratory has a configuration that enables the principle of the "walking forward" of the processing of a sample, namely a first area in which the sample to be analyzed is inserted into the laboratory and enters the analytical area, an area in which the step of transferring the absorbent body in the container comprising the PCR amplification reaction mixture of nucleic acids is carried out, and an area in which the PCR is performed in the thermocycler, contacting the amplification products with the sequencing reaction mixture, and sequencing.

A fourth object of the present invention is the use of a device according to the invention for sampling biological material from a biological trace having any surface from a micro-surface of the order of 1 mm$^2$ or having any volume, from a micro-volume of the order of 1 microliter.

According to one feature of the invention, if the sampling is performed with the device directly on a human, said human being not living.

According to a feature of the invention, if the sampling is performed with the device indirectly on a human, said human can be living. Indirectly means the use, upstream of the sample, of a self-piercing pen-type tool used for example for verifying the blood glucose level of an individual from a blood drop. The use of the self-piercing artificial pen is on a part of the body of the living individual, in particular a finger of the hand, causes a drop of blood to be generated at the puncture area. This blood drop is then transferred to a strip, known to those skilled in the art, by wiping or simple capillary action.

A fifth object of the invention is a method of collecting biological material, characterized in that it comprises a step of contacting the device according to the invention with said biological material.

By contacting the device with the biological material, it is meant according to the present invention the wiping of the support on which said biological material is located using movements of horizontal scans, or by simple buffered or capillary action depending on the nature of the surface to be wiped.

When the biological material to be collected is wet, the collection is performed directly, and when the biological material is in dry form, said method may comprise a prior step of humidifying said absorbent body of the device or humidifying said biological material, with sterile and/or apyrogenic water.

Preferably, the absorbent body or biological material is not directly wetted prior to collection. The area on which the biological material to be collected is located can then be subjected to a controlled local hygrometry that promotes the separation of the biological material from its support thereby facilitating its collection.

When the biological material to be collected is a dry, invisible contact trace, such as epithelial cells present on the stock of a firearm or the handle of a knife, said collection method may comprise a prior step of wetting the absorbent body of the device as well as biological material with sterile and/or apyrogenic water. Through a vacuum type laboratory suction system or vacuum pipette, known by those skilled in the art, the continuous air pressure generated by the system allows to draw the biological material from its bearing support to be attached directly to said absorbent body used herein as a membrane, a filter of the suction system.

Advantageously according to the invention, a very small amount of sterile and/or apyrogenic water is provided, preferably sterile and apyrogenic, is required for said humidification, of from about 1 to about 50 microliters, preferably from about 1 to about 20 microliters, preferably between about 0.5 and 5 microliters.

A sixth object of the present invention is a method for collecting and analyzing and/or identifying nucleic acids of a biological material, characterized by comprising:

1. The step(s) of the method for collecting said biological material according to the invention,
2. A step of amplifying the nucleic acids, preferably DNA, of said biological material collected on the absorbent body of the device comprising contacting said absorbent body comprising biological material collected with at least one PCR amplification reaction mixture of nucleic acids, preferably DNA, the PCR amplification reaction;

3. A step of sequencing the nucleic acids amplified in step 2 comprises contacting said nucleic acids with a sequencing reaction mixture, sequencing and analyzing the sequencing result.

The analysis method according to the present invention implementing the device according to the invention has the advantage of being able to go from step 1. of collection of the biological material to step 2. of amplification of the nucleic acids of said biological material, without the need for another step, in particular a step of cell lysis and/or extraction of the nucleic acids.

Moreover, without delay, after collection, the nucleic acids, in particular DNA, trapped in the absorbing body of the device are directly amplified by PCR (Polymerase Chain Reaction), without adding an additive to stabilize the reaction of amplification, for example for the determination of human genetic profiles.

Thus, no additive, reagent or additional step is to be added between the sampling and amplification of DNA with the commercial kits (such as Identifiler plus, Identifiler direct, GlobalFiler et GlobalFiler express of the Thermofisher company)

By way of example, the composition of the Identifiler kit is as described in the FIG. 5.

These kits can therefore be used without modification of their initial composition, in particular without additional component additions, which is a very significant gain in terms of cost and time.

In addition, the small area of the absorbent body allows not only to reduce the reaction volume required for amplification with respect to that recommended by the providers, maintaining the same proportions between the different reagents thus generating significant savings, but also allows to limit the alteration of the trace thereby promoting its preservation for subsequent analyses.

The PCR amplification reaction mixture of nucleic acids as used in step 2. of the method of the present invention refers to a particular combination of reagents which are needed to perform a PCR amplification reaction. The amplification reaction mixture used in each case and the conditions applied to carry out the amplification are well known to those skilled in the art. For example, the amplification reaction mixture may include one or more sets of primers for ensure that a particular target nucleic acid is subjected to the amplification reaction, as well as enzymes, nucleotides, probes, salts and buffers that may also be needed to perform amplification.

Said nucleic acid PCR amplification reaction mixture is added in an amount sufficient to saturate the absorbent body of the device according to the invention. It is typically added in an amount of 7.5 to 25 microliters, preferably 12.5 to 15, more preferably 12.5 microliters.

Said nucleic acid sequencing reaction mixture as used in step 3. of the method of the present invention refers to a particular combination of reagents which are needed to perform sequencing of amplified DNA fragments. The sequencing reaction mixture used in each case and the conditions applied to perform sequencing by the electrophoresis technique are well known to those skilled in the art. For example, mixing the sequencing reaction may include formamide and a set of known molecular weight DNA fragments, commonly referred to as the size standard by the person skilled in the art. Based on the assigned size, each amplified DNA fragment is identified by comparing with a set of reference DNA fragments commonly referred to as allelic ladder by those skilled in the art.

According to one possible embodiment of the invention, the analysis step can be carried out directly or indirectly. In particular, for indirect analysis, if the device according to the present invention comprises an absorbent body composed of synthetic fibers, preferably made of flocked Nylon, the biological material taken from step 1. can be released by contacting with a sterile water volume of 5 to 20 microliters, preferably 5 to 10 microliters, then a volume of said water comprising the nucleic acids thus released from the absorbent body is taken out for performing the step 2. of amplification. Preferably, the volume thus taken is 5 microliters.

The method for collecting and analysing and/or identifying the nucleic acids of a biological material implementing the device according to the invention requires only very few steps compared to the methods conventionally used for such analyses and or identification, enabling it to be carried out as close as possible to the collection points, in a single mobile laboratory, such as, for example, a van-type vehicle, in which at least two 96-well plate-type containers can be found, a nucleic acid PCR amplification reaction medium, a thermocycler, a sequencing reaction mixture, and a sequencer.

Thanks to its very low contact surface and its properties described above, the device according to the invention can advantageously be used with a miniature device for biological detection and/or miniaturized genetic analysis of the Lab-on-chip type, preferably using a microfluidic technique.

The accompanying drawings illustrate the invention:

FIG. 5 is the composition of the IdentiFiler Kit as marketed in 2015.

Other features and advantages of the invention may appear in the following examples, and are given purely by way of non-limiting illustration.

EXAMPLES

Example 1

Determining the Optimal Surfaces-Matrix of Cellulose

In order to test the effect of the size on the collection efficiency, analysis and identification of DNA, it has been carried out at the following test:

A dry solid absorbent body consisting of a dry cellulose matrix comprising FTA-type surfactant and denaturant agents (GE company) or NucleiCard (COPAN company), in the form of a disk (referred to as "biological pellet") of a diameter of 1.2 mm (i.e. a surface of 1.13 mm$^2$), 2 mm (i.e. a surface of 3.14 mm$^2$), 3 mm (i.e. a surface of 7.06 mm$^2$) and a square of 3.3 cm on the side (i.e. a surface of 10 mm$^2$) were tested.

In the absence of an industrial collection device, which is an object of the present invention, namely said absorbent body attached to a rod, the biological pellet is manipulated using a tweezers type clamp. It is noted that the users have a difficulty of use not allowing the use to be imagined, in particular by police forces on crime scenes. The experimental collection method is decomposed in the following manner: collecting the biological trace by wiping the support using horizontal or circular movements, or by simple buffering depending on the nature of the surface to be wiped.

Tests have been performed on different types of traces likely to present DNA in varying amount and quality but mainly degraded. To this end, the collections have been made on so-called "contact" traces (wiping of different media such as the interior of a vehicle or daily objects), blood traces, buccal cells and diverse biological tissues (body elements in advanced degradation states such as putrefaction or carbonization) with each time a 1 microliter sample. The absorbent body is used dry without wetting the trace or absorbent body prior to collection.

After collection, the absorbent body is brought into contact with one STR (Short Tandem Repeat) type DNA fragment amplification reaction medium such as identification Identifiler plus and Globalfiler (Lifetechnologies) kits and then inserted into the thermocycler for PCR.

Thus, without delay, at the end of collection, the DNA trapped in the biological pellet is directly amplified by PCR (Polymerase Chain Reaction) in a thermocycler (GeneAmp PCR system 9700), without adding an additive to stabilize the amplification reaction, to determine human genetic profiles. This amplification reaction is carried out using commercial kits for amplification of STR-type DNA fragments (Short Tandem Repeat) such as Identifiler plus and Globalfiler kits (Lifetechnologies) according to the recommendations of the provider. Thus, in the case of use of Identifiler plus, the thermocycler is used with 28 PCR cycles and with Globalfiler with 29 PCR cycles.

Genotyping of the PCR products is then performed using the ABI 3500 xl (Lifetechnologies) analyzer. Analysis of the results is performed using the GeneMapper ID-X version 1.2 Software The results obtained show that the surfaces of 10 mm$^2$ and 7.06 mm$^2$ do not allow to identify the DNA profile of the sample, matching the generally accepted idea by those skilled in the art that a microtrace DNA sample of the order of 1 microliter cannot be collected and analyzed with such collection devices.

However, and this is a part of the technical solution of the present invention, the applicant has surprisingly and unexpectedly discovered that by further decreasing the surface area of the biological pellet, by performing the same tests with smaller absorbent body surfaces, of 1.13 to 3.14 mm$^2$ it was possible to obtain a partial DNA profile (50% of the identified alleles) in the case of the surface of 3, 14 mm$^2$ and even a complete DNA profile (100% of the identified alleles) with the surface of 1.13 mm2, against the technical prejudice of the person skilled in the art. Thus, the applicant has shown that it was not only possible to collect but also to analyze and accurately identify a microtrace of DNA of the order of 1 microliter, using a collection device.

In order to validate the effectiveness of the rapid analysis process, biological traces have also been collected using a conventional swab device (FloqSwab, COPAN company) in amounts of 1, 3 and 5 microliters, and then analyzed with the aid of the Identifiler Plus, Identifiler Direct and GlobalFiler kits, according to the provider recommendations without pre-quantification of the DNA extracted from the entirety of the end of the swab.

Figure 6A:
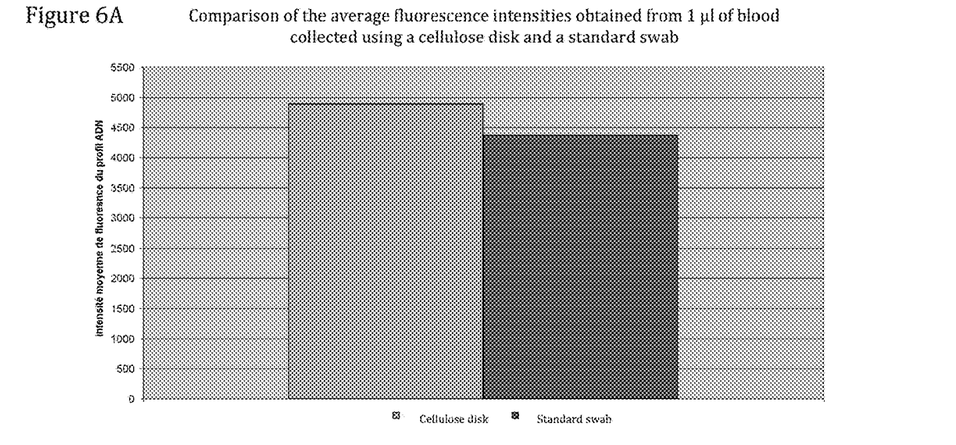
FIG. 6A is the comparison of the average fluorescence intensities obtained from 1 microliter of collected blood using a cellulose disk (to the left) and a standard swab (right).

The results obtained from the rapid analysis process, subject of the present invention, are better than those obtained using the conventional analysis process, with a step of cell lysis and obligatory extraction (FIG. 6A). Indeed, the rapid collection and analysis system is mainly more efficient on the biological traces of very small areas and volumes (microtraces of the order of 1 mm$^2$ and 1 µl) due to the miniaturization of the collection surface and the absence of loss of genetic material (due to the absence of DNA extraction from the collection device).

Example 2

Determining the Optimal Composition of the Absorbent Body—Cellulose Disk/Flocked Synthetic Fiber—Surface 1.13 mm$^2$ Comparative performance tests are performed between an absorbent body composed of a cellulose disk of 1.13 mm$^2$ comprising denaturing and surfactants agents and synthetic fibers of a total surface of 1.13 mm$^2$ flocked on a rod and comprising these same denaturing agents and surfactants.

Figure 7:
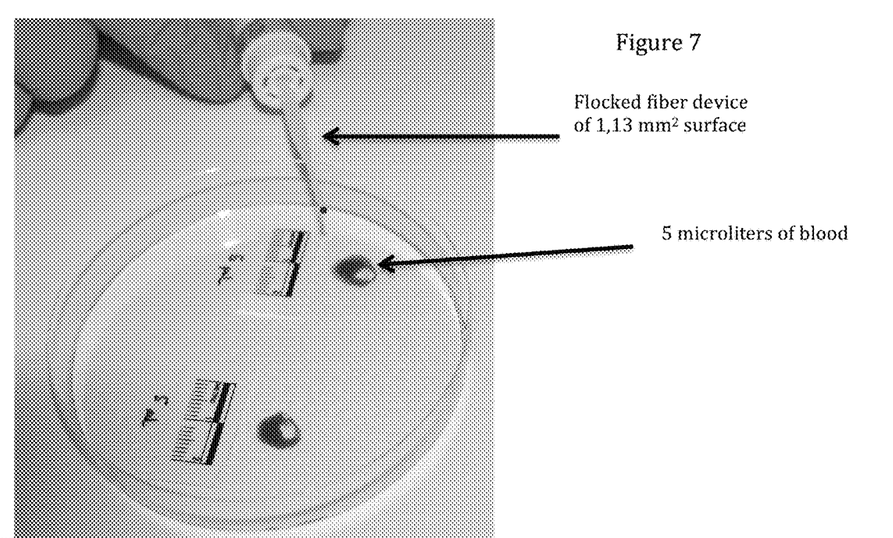
FIG. 7 is a photograph of 2 drops of blood of 5 microliters taken with the device according to the invention (surface 1.13 mm$^2$).

Two types of traces are collected:
A blood trace from 5 µl of blood on a glass blade (FIG. 7)
A semen trace from 1 µl of dried semen onto a glass blade.

Directly after collection, the absorbent bodies are deposited in the wells of a 96 well microplate containing 25 µl of amplification reaction mixture of STR type DNA fragments (Short Tandem Repeat) provided with the GlobalFiler (Lifetechnologies) kit, then the microplate is inserted into a thermocycler (Gene Amp PCR System 9700) for the PCR reaction. Genotyping of the PCR products is then performed using the ABI 3500 XL sequencer analyzer (Lifetechnologies). The analysis of the reagents is carried out using the software GeneMapper ID-X version 1.2.

Figure 6B:
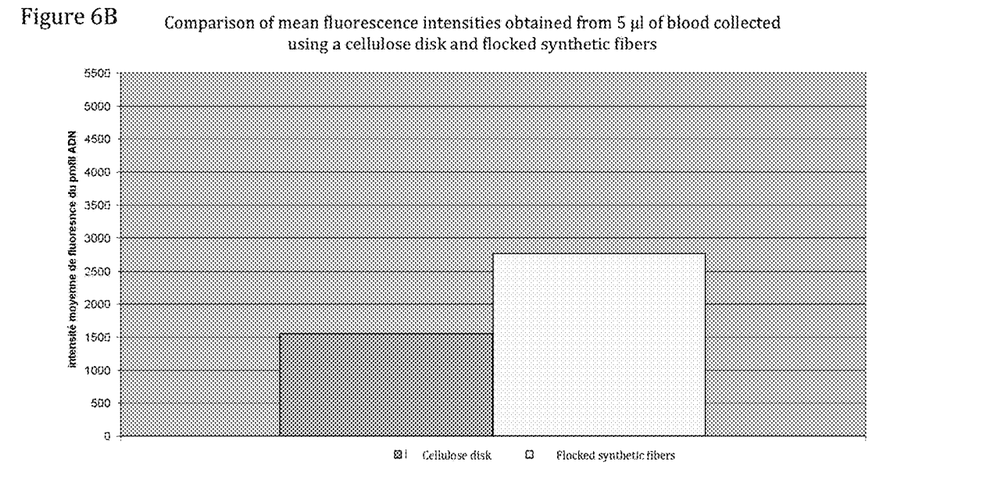
FIG. 6B is the comparison of the average fluorescence intensities obtained from 5 microliters of collected blood using a cellulose disk (to the left) and synthetic fibers flocked on a rod (to the right).
Figure 6C:
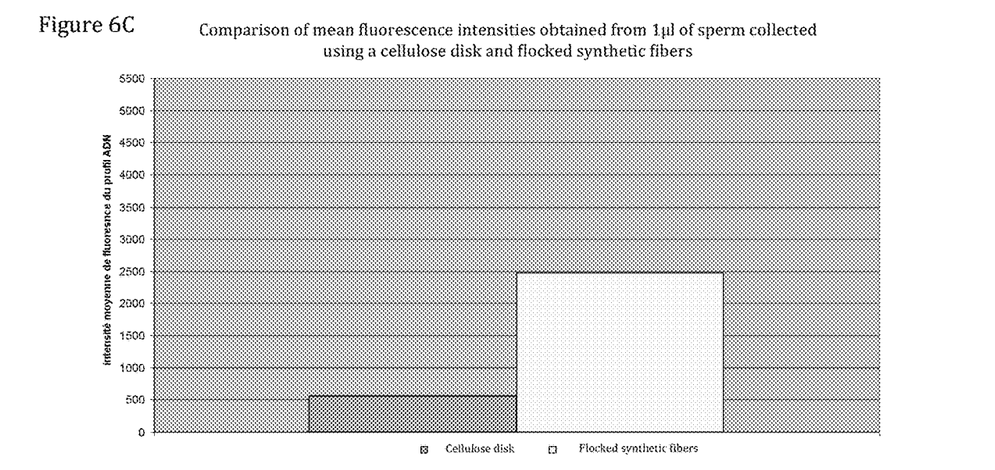
FIG. 6C is the comparison of the average fluorescence intensities obtained from 1 microliter of semen collected using a cellulose disk (to the left) and synthetic fibers flocked on a rod (to the right).

The results allow to identify identical DNA profiles with cellulose and flocked synthetic fibers, namely an identification of 100% of the DNA profile of the blood and semen samples. In contrast, the flocked synthetic fibers device is more effective than cellulose disk device as the mean fluorescence intensity obtained from the genetic profile with the flocked fibers is greater than that obtained with the cellulose disc (FIGS. 6 B and 6C).

Figure 9:
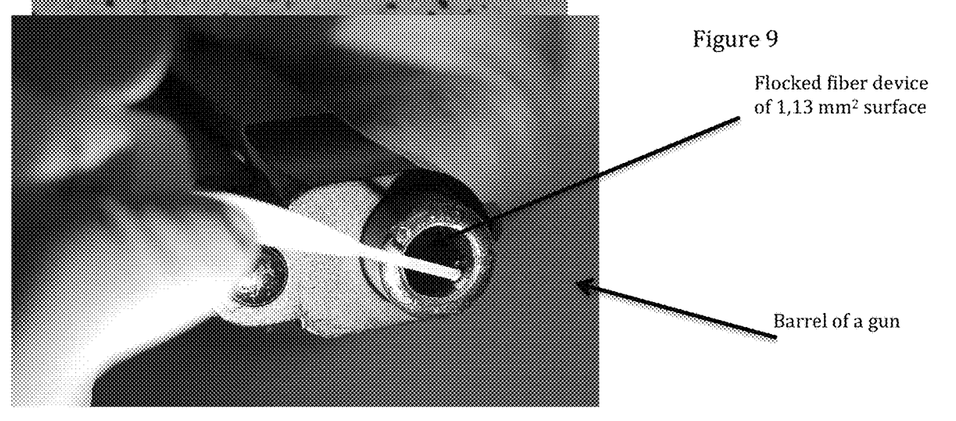
FIG. 9 photographs a microliter blood trace present in the barrel of a firearm and taken with the device according to the invention (surface 1.13 mm$^2$).

In addition, a real comfort of use was noted with the flocked synthetic fibers version of the device, in comparison with the cellulose disk device manipulated using tweezers, especially when the trace to be collected is difficult to access as may be the case inside the barrel of a gun (FIG. 9).

Example 3

Verification of the Performance of the Flocked Synthetic Fibers Device of 1.13 mm$^2$ and Treated with Denaturing and Surfactants Agents with Respect to a Standard Swab (4N6 FloqSwab, Marketed by the Company COPAN)

Comparative efficacy tests are performed between the synthetic fiber with a total area of 1.13 mm2 flocked onto a rod and comprising denaturing and surfactants agents.

Two types of traces are collected:
1. a thumbprint revealed on a glass
2. a bloody thumbprint revealed on the floor (tiles)

In the case 1. The upper part of the thumbprint is collected with the device of flocked synthetic fibers while the lower part of the thumbprint is collected with a standard swab.

In the case 2. wiping with the flocked synthetic fibers of 1.13 mm$^2$ allowed to collect only the biological material materialized by two ridges papillary drawing due to the small area of the device. In contrast, 5 ridges were collected with standard swab altering especially the papillary drawing.

Directly at the end of the collection, the absorption bodies are placed in the wells of a 96-well microplate containing 25 μl of STR (Short Tandem Repeat) type DNA fragments amplification reaction mixture supplied with the GlobalFiler kit (Lifetechnologies), then the plate is inserted in a thermocycler (Gene Amp PCR System 9700) for PCR reaction. Genotyping of the PCR products is then performed using the analyzer ABI 3500 XL sequencer (LifeTechnologies). Analysis of reagents is carried out with the GeneMapper ID-X version 1.2 software. The sample taken by means of the rapid analysis method from flocked synthetic fibers of 1.13 mm$^2$ on the papillary traces revealed on glass yielded a better result than that obtained using the method of conventional analysis with cell lysis step and required extraction. Indeed, a full DNA profile was obtained from the quick analysis process while a very partial DNA profile was obtained from the standard analysis process.

Figure 8:
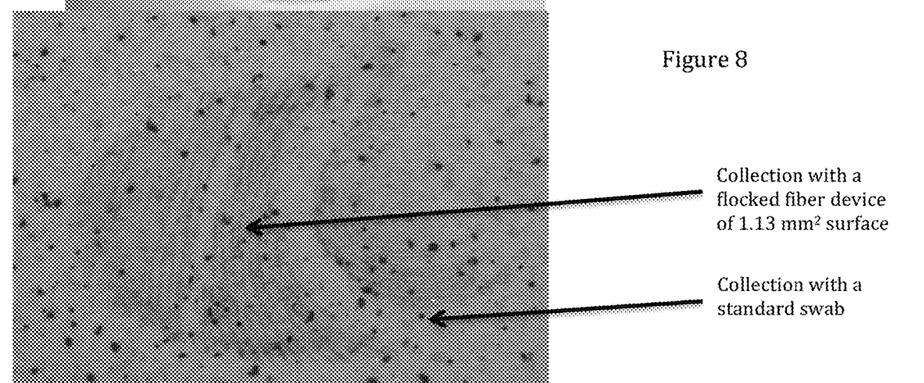
FIG. 8 is a fingerprint of blood taken from a standard swab and with the device according to the invention (surface 1.13 mm$^2$).

Samples taken from the bloody thumbprint allowed to obtain a complete DNA profile to mean intensities of fluorescence equivalent between the two gathering and analysis devices. In contrast, the ability to collect only two peaks of the papillary drawing using the collection and rapid analysis device instead of 4 to 5 peaks with the collection and analysis device for an equivalent result demonstrates all the sensitivity and interest of the collection and rapid analysis device to limit the alteration of the trace (FIG. 8).

The invention claimed is:

1. A device for collection of biological material, characterized in that it comprises a rod having at least at one end a dry absorbent body of an area of from 1 to 3.14 mm$^2$, said absorbent body comprising surfactants and denaturing agents.

2. The device according to claim 1, characterized in that said end having said absorbent body is scored or ejectable.

3. The device according to claim 1, characterized in that said absorbent body is selected from the group consisting of cellulose, cotton, flocked synthetic fibers, hydrophilic polymers, fiberglass, Polytetrafluoroethylene and a porous ceramic.

4. The device according to claim 1 characterized in that said biological material is selected from the group consisting of physiological body fluids, cells or cell suspensions of humans or animals, in particular a contact trace, blood, bone marrow, buccal cells, semen, saliva, cervical fluid, hair, hair, skin, muscle, serum, synovial fluid, cerebral spinal fluid, lymphatic fluid, vaginal cells, urine, feces, and more generally, any human or animal biological tissue degraded or not;

physiological body fluids or cell suspensions of plants; liquid products, extracts or suspensions of bacteria, fungi, plasmids, parasites, or viruses; liquid extracts or homogenates of human or animal body tissue; media from a nucleic acid synthesis; and mixtures of nucleic acids synthesized chemically or biochemically.

5. The device according to claim 1 characterized in that it comprises a hermetic case.

6. A method of collecting biological material, characterized in that it comprises a step of contacting the device according to claim 1 with said biological material.

7. The method for collection of biological material according to claim 6 characterized in that when the biological material to be collected is wet, the collection is performed directly, and when the biological material is in dry form, said process comprises a prior step of humidification of said absorbent body of the device or the humidification of said biological material with sterile water and/or pyrogen free.

8. The method of claim 6, wherein the method comprises contacting a biological trace having any surface from a micro-area of the order of 1 mm$^2$ or having any volume, from a micro-volume of 1 microliter.

9. The method of claim 6, wherein the biological material is a human sample.

10. The method of claim 9, wherein the human sample is obtained by contacting a human with the device.

11. The method of claim 10, wherein the contacted human is not alive.

* * * * *